(12) United States Patent
Matsunaga et al.

(10) Patent No.: US 8,696,657 B2
(45) Date of Patent: Apr. 15, 2014

(54) TREATMENT TOOL

(75) Inventors: Rei Matsunaga, Tokyo (JP); Masahiro Ishikawa, Tokyo (JP)

(73) Assignee: Olympus Medical Systems Corp. (JP)

( * ) Notice: Subject to any disclaimer, the term of this patent is extended or adjusted under 35 U.S.C. 154(b) by 794 days.

(21) Appl. No.: 12/340,861

(22) Filed: Dec. 22, 2008

(65) Prior Publication Data

US 2010/0160727 A1      Jun. 24, 2010

(51) Int. Cl.
   *A61B 18/04*      (2006.01)
   *A61B 18/18*      (2006.01)

(52) U.S. Cl.
   USPC .............................................. 606/28; 606/41

(58) Field of Classification Search
   USPC ................. 606/27–52; 604/524, 525
   See application file for complete search history.

(56) References Cited

U.S. PATENT DOCUMENTS

| | | | | |
|---|---|---|---|---|
| 5,533,985 | A * | 7/1996 | Wang | 604/264 |
| 6,053,913 | A | 4/2000 | Tu et al. | |
| 6,375,650 | B1 * | 4/2002 | Ouchi | 606/1 |
| 2005/0267459 | A1 | 12/2005 | Belhe et al. | |
| 2006/0084969 | A1 | 4/2006 | Truckai et al. | |

FOREIGN PATENT DOCUMENTS

| | | |
|---|---|---|
| JP | 63-139726 | 6/1988 |
| JP | 08-057035 | 3/1996 |
| JP | 08-196620 | 8/1996 |
| JP | 10-045988 | 2/1998 |
| JP | 2000-342595 | 12/2000 |
| JP | 2008-279107 | 11/2008 |

OTHER PUBLICATIONS

International Search Report mailed Jan. 26, 2010 in related PCT International Application No. PCT/JP2009/071325.
Office Action issued by the Japanese Patent Office on Jul. 6, 2010 in connection with corresponding Japanese Patent Application No. 2010-507748.
English translation of Japanese Office Action issued in connection with Japanese Patent Application No. 2010-507748 on Jul. 6, 2010.
Search Report issued by European Patent Office on Jul. 31, 2012 in connection with corresponding European patent application No. EP 09 83 4880.

* cited by examiner

*Primary Examiner* — Nicholas Lucchesi
*Assistant Examiner* — Leah Stohr
(74) *Attorney, Agent, or Firm* — Ostrolenk Faber LLP

(57) ABSTRACT

A treatment tool for an endoscope which is transendoscopically inserted into a body cavity for use, and which includes: a sheath at least partially composed of mixed material in which thermoplastic resin and a crosslinking promoter are mixed; a manipulation wire inserted through the aforementioned sheath so as to be capable of advancing and retracting; a treatment part attached to a first end of the aforementioned manipulation wire; and a manipulation part attached to a second end of the aforementioned manipulation wire; wherein said sheath has a crosslinked part where said thermoplastic resin is crosslinked by irradiating said mixed material with ionizing radiation, and a non-crosslinked region where said thermoplastic resin is not crosslinked.

6 Claims, 10 Drawing Sheets

|  | Scission temperature | Non-scission temperature |
|---|---|---|
| Sample 1 | 230°C | 200°C |
| Sample 2 | 250°C | 230°C |
| Sample 3 | 280°C | 250°C |
| Sample 4 | NA | 300°C |

FIG. 5

|  | Compression distance (average) |
|---|---|
| Sample 5 | 7.0mm |
| Sample 6 | 2.9mm |
| Sample 7 | 6.3mm |

FIG. 6

|  | Insertable distance | | |
|---|---|---|---|
|  | Test subject 1 | Test subject 2 | Test subject 3 |
| Sample 5 | 7cm | 6cm | 7cm |
| Sample 7 | 6cm | 5cm | 5cm |
| Sample 6 | 8cm | 7cm | 9cm |

|  | Pass-through force (average) |
|---|---|
| Sample 5 | 0.6502N |
| Sample 6 | 0.6814N |
| Sample 8 | 0.2472N |
| Sample 9 | 0.3292N |

| | Force |
|---|---|
| Sample A | 2.35N |
| Sample B | 4.62N |

TREATMENT TOOL

BACKGROUND OF THE INVENTION

1. Field of the Invention

The present invention relates to a treatment tool for an endoscope which is transendoscopically inserted into a body cavity for use.

2. Description of Related Art

Heretofore, various types of endoscopic treatment tools have been known which are transendoscopically inserted for use into the body cavities of patients and the like. The general configuration of such endoscopic treatment tools is as follows. That is, various types of treatment parts such as forceps for the conduct of treatment are provided at the distal end of a flexible, elongated tubular member (sheath). The treatment part is connected to the first end of a manipulation wire inserted through a sheath, and is manipulated via a manipulation part connected to the second end. The treatment part and the sheath are then inserted into a body cavity, and the treatment part reaches the site subject to treatment, where a treatment procedure or the like is conducted.

SUMMARY OF THE INVENTION

The present invention is a treatment tool for an endoscope which is transendoscopically inserted into a body cavity for use, and which includes: a sheath at least partially composed of mixed material in which thermoplastic resin and a crosslinking promoter are mixed; a manipulation wire inserted through the sheath so as to be capable of advancing and retracting; a treatment part attached to a first end of the manipulation wire; and a manipulation part attached to a second end of the manipulation wire; wherein said sheath has a crosslinked part where said thermoplastic resin is crosslinked by irradiating said mixed material with ionizing radiation, and a non-crosslinked region where said thermoplastic resin is not crosslinked.

BRIEF DESCRIPTION OF THE DRAWINGS

FIG. 5 is a table which shows study results pertaining to the compression resistance of a crosslinked part.

FIG. 6 is a table which shows study results pertaining to the buckling resistance of a crosslinked part.

PREFERRED EMBODIMENTS

Figure 1:
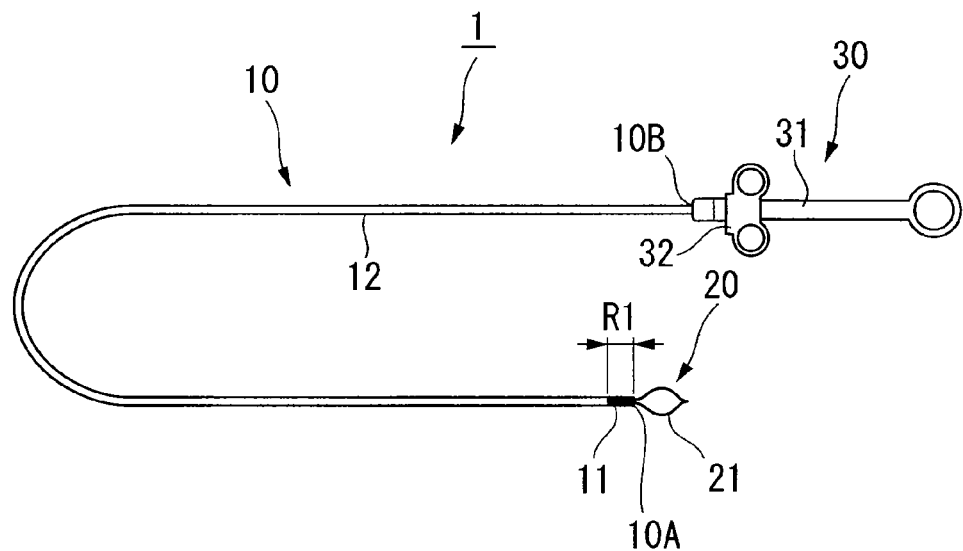
FIG. 1 is a figure which shows the medical treatment tool of a first embodiment of the present invention.

A first embodiment of the present invention is described with reference to FIG. 1 to FIG. 8. FIG. 1 is a figure which shows a medical treatment tool (hereinafter, simply "treatment tool") 1 of the present embodiment.

The treatment tool 1 is provided with an elongated sheath 10 which is inserted into a body cavity, a manipulation wire (not illustrated in the figures) which runs through and within the sheath 10, a treatment part 20 which is connected to a first end of the manipulation wire, and a manipulation part 30 which is connected to the sheath 10.

The sheath 10 is a flexible, tubular member, and a range R1 of prescribed length from a first end 10A on the treatment part 20 side constitutes a crosslinked part 11 of higher rigidity than other parts. The remaining region of the sheath 10 constitutes a below-mentioned non-crosslinked region 12. A second end 10B of the sheath 10 is connected to the manipulation part 30 by adhesion or welding.

In the following description of the treatment tool 1, the side on which the treatment part 20 is disposed is referred to as the distal end side, and the side on which the manipulation part 30 is disposed is referred to as the proximal end side. The structure and physical properties of the crosslinked part 11, and method of forming the crosslinked part 11 in the sheath 10 are discussed below.

A snare wire 21 constituting the treatment part 20 is a member of publicly known which is used when excising polyps and the like, and is connected to the distal end (first end) of the manipulation wire which is passed through and within the sheath 10 so as to be capable of advancing and retracting. Accordingly, it is possible to house the snare wire 21 inside the sheath 10 by sliding the manipulation wire to the proximal end side.

The manipulation part 30 is provided with a body 31 to which the sheath 10 is connected, and a slider 32 attached to the body 31 so as to be capable of sliding in the longitudinal direction of the body 31. A space such as a groove or slit or the like which is not illustrated in the drawings extends in the longitudinal direction in the body 31, and the proximal end (second end) side of the manipulation wire which runs through and within the sheath 10 enters the pertinent space. The proximal end of the manipulation wire is connected to the slider 32.

A plug (power supply part) which is not illustrated in the drawings is provided in the slider 32, and it is possible to supply high-frequency current to the treatment part 20 via the manipulation wire by connecting the plug and a high-frequency power source not illustrated in the drawings.

Next, a detailed description is given of the sheath 10 and the crosslinked part 11.

The sheath 10 is formed with use of thermoplastic resin. As thermoplastic resin which may be used, one may suitably employ, for example, thermoplastic aromatic-ether aromatic-ester resin, thermoplastic ether amide resin, and so on, but one is not limited to these. Moreover, one may use a single type of resin alone, or a blend of multiple types of resin.

A variety of properties are required of the sheath 10 which is inserted into a body cavity. In particular, the following properties are required in the case of an endoscopic treatment tool which passes through and within a channel provided in the insertion part of the endoscope and which is transendoscopically inserted into a body cavity. That is, the capability of satisfactory insertion even when the channel meanders inside the body cavity (insertability); the transmission of manipulations to the distal end without bending of the sheath when push-in manipulation of the sheath is conducted (buckling resistance); the inhibition of compression in the axial direction when performing push-in manipulation, and inhibition of attenuation of the force generated in conjunction with push-in manipulation, as well as efficient transmission without attenuation when transmitting the force generated by the manipulation part (e.g., the force with which the slider 32 is pulled) as force used in treatment by the treatment part 20 at the distal end (e.g., the force with which tissue is clamped or tightly bound) (compression resistance); and the prevention of melting and deformation from the heat generated when high-frequency current is supplied for use to the treatment part (heat resistance), and so on.

Some of these parameters stand in contradictory relation to each other so that when some are improved, others are worsened. For example, one may cite the example that when the rigidity of the sheath is increased, buckling resistance improves, but insertability declines. Accordingly, it is not easy to manufacture the sheath in such a way that all parameters are suitably set.

It is known that, by adding a crosslinking promoter to thermoplastic resin and irradiating it with ionizing radiation, the molecules of the thermoplastic resin are crosslinked, and the rigidity of the resin is improved. Thus, the sheath 10 of the present embodiment is formed using mixed material in which a crosslinking promoter is intermixed with the thermoplastic resin, and a crosslinked part 11 is further formed by subjecting the desired part to irradiation with ionizing radiation.

As the employed crosslinking promoter, one may use, for example, various types of multifunctional monomers. As specific examples, one may cite diacrylate compounds such as diethylene glycol; dimethacrylate compounds such as ethylene glycol dimethacrylate; triacrylate compounds such as trimethylol propane triacrylate; trimethacrylate compounds such as trimethylol propane trimethacrylate; triallyl cyanurate compounds such as triallyl isocyanurate and triallyl cyanurate; diallyl malate, diallyl fumarate, epoxy acrylate, and so on. Among these, triallyl isocyanurate, triallyl methaisocyanurate, and epoxy acrylate are particularly preferable from the standpoint of obtaining resin compositions with both high compression resistance and high heat resistance. These may each be used alone, or they may be used in combinations of two or more. The proportion of use of the crosslinking promoter is 1 to 20 parts by mass—and preferably 3 to 10 parts by mass—relative to 100 parts by mass of thermoplastic aromatic ether ester resin. The crosslinking promoter may be selected within this range according to the required heat resistance performance or the like.

Figure 2:
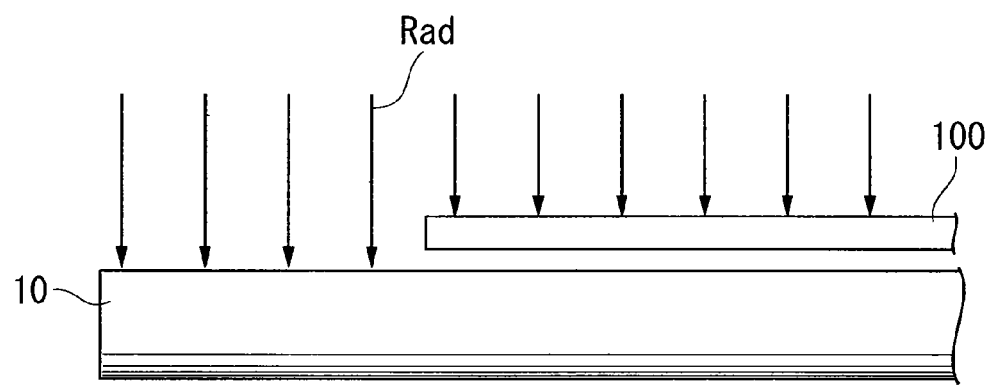
FIG. 2 is a figure which shows the operations for forming a crosslinked part in the sheath of this same medical treatment tool.

As the ionizing radiation employed in the present invention, one may cite electron beam and accelerated electron rays as well as γ-rays, X-rays, α-rays, γ-rays, ultraviolet beam, and so on. It is preferable to use accelerated electron beam and γ-rays from the standpoint of industrial utility—e.g., convenience of radiation source, transmission thickness of ionizing radiation, and speed of crosslinking treatment. The voltage of the accelerated electron beam may be appropriately selected according to the thickness of the sample. As to the irradiation dose of ionizing radiation, in the case of electron beam, for example, it would be sufficient to set the irradiation dose at 10-500 kilogreys (kGy), and preferably 50-300 kGy. If this irradiation dose is less than 10 kGy, the proportion of crosslinked sites in the irradiated region tends to be small, and heat resistance tends to be insufficiently imparted, while at more than 500 kGy, physical properties tend to decline due to molecular fragmentation. In the present embodiment, the crosslinked part 11 is formed by conducting irradiation with electron beam of 300 kGy When forming the crosslinked part 11 in the sheath 10, as shown in FIG. 2, the area which is not to be crosslinked is covered with a shield 100 composed of lead or the like, and irradiation with ionizing radiation Rad is then conducted. As a result, the region irradiated with the ionizing radiation Rad becomes the crosslinked part 11, while the region covered by the shield 100 becomes the non-crosslinked region 12 in which crosslinking does not occur and the properties of thermoplastic resin are retained. Accordingly, it is possible to form the crosslinked part 11 in the desired location and to the desired length of the sheath 10 by appropriately selecting the position and length of the region covered by the shield 100.

With respect to the sheath 10 of the present embodiment, after covering it with the shield 100 except for an exposed region R1 of prescribed length from the distal end, the crosslinked part 11 is formed by conducting irradiation with ionizing radiation Rad.

Furthermore, within a range that does not impair the purpose of the present invention, it is also acceptable to add as necessary hydrolysis inhibitors, processing stabilizers, inorganic fillers, colorants such as carbon black, nuclear agents, oxidation inhibitors, ultraviolet absorbing agents, antistatic agents, lubricants, plasticizers, flame retardants and the like.

The results of study concerning the various physical properties of the crosslinked part 11 produced in the above-described manner are shown below.

A) Study of Heat Resistance

The following four samples were prepared. The form of each sample was that of a sheet with a thickness of 0.3 millimeters (mm).

Sample 1: Thermoplastic aromatic-ether aromatic-ester resin to which 5 parts by weight of triallyl isocyanurate were added.

Sample 2: Thermoplastic aromatic-ether aromatic-ester resin to which 5 parts by weight of triallyl isocyanurate were added, and which was irradiated with electron beam of 50 kGy.

Sample 3: Thermoplastic aromatic-ether aromatic-ester resin to which 5 parts by weight of triallyl isocyanurate were added, and which was irradiated with electron beam of 100 kGy.

Sample 4: Thermoplastic aromatic-ether aromatic-ester resin to which 5 parts by weight of triallyl isocyanurate were added, and which was irradiated with electron beam of 300 kGy.

Each sample 1 to 4 was formed to a width of 6 mm and a length of 50 mm, with the two ends in the lengthwise direction held by a measuring device. Next, heated bodies of copper of 0.3 mm thickness and heated to various temperatures were set in jigs, and the heated body was held above the vicinity of the center of the sample in the lengthwise direction using a weight of prescribed weight and so as not to contact the sample. As to the temperatures of the heated bodies, the 5 types of 200° C., 230° C., 250° C., 280° C., and 300° C. were prepared.

Next, holding by means of weights was stopped, and the heated bodies were brought into contact with the samples at a load of 1 newton (N) for a maximum period of 30 seconds. While exchanging the heated bodies in sequence from the lowest temperature, the temperature at which melting and scission of the sample occurred was treated as the scission temperature, and the highest temperature among the temperatures at which scission did not occur was treated as the non-scission temperature. The results are shown in FIG. 3.

Figures 3, 4:
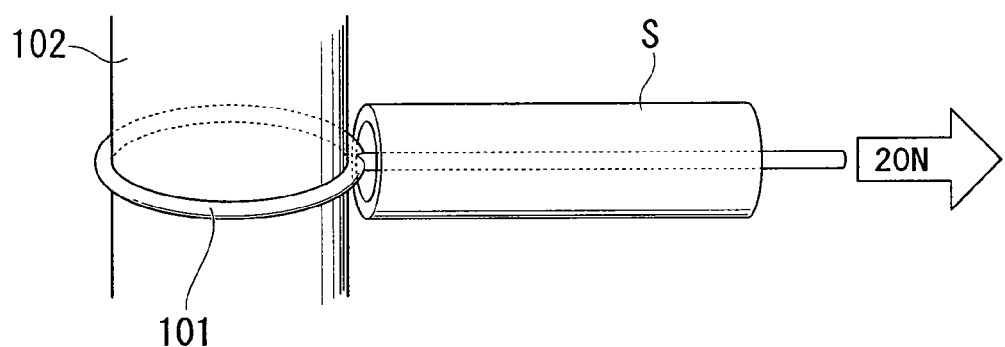
FIG. 3 is table which shows study results pertaining to the heat resistance of a crosslinked part.
FIG. 4 is a figure which shows the study method pertaining to the compression resistance of a crosslinked part.

As shown in FIG. 3, compared to sample 1 where irradiation with electron beam constituting one type of ionizing radiation was not conducted, it was demonstrated that heat resistance was improved in samples 2 through 4 which were subjected to crosslinking treatment. It was also confirmed that heat resistance stood in a proportional relation to the irradiation dose of electron beam. The NA of sample 4 indicates that even when a heated body of 300° C. made contact for 30 seconds, no scission occurred.

B) Study of Compression Resistance

FIG. 4 is a figure which shows the methodology of this study. Wires 101 having a loop-shaped tip with a loop diameter of 25 mm were passed through and within sheath-like (tubular) samples 5 to 7 (indicated by the code S in FIG. 4) having an external diameter of 2.4 mm, an internal diameter of 1.6 mm and a length of 50 mm until the loop projected from the distal end side of the sample S, after which a metal column 102 of 15 mm diameter was passed through the loop. Next, with the proximal end side of the sample S fixed in place with a jig which is not illustrated in the figure, the wire 101 was pulled nearer to the proximal end side at 20 N. As the metal column 102 was pulled nearer by pulling the wire 101 nearer, and as the sample S was compressed between its proximal end and the metal column 102, the differential in the length of the sample S before and after compression was measured as the amount of compression. The composition of each sample 5 through 7 was as follows.

Sample 5: polytetrafluoroethylene (PTFE: a base material often used in the tube sheaths of conventional endoscopic treatment tools)

Sample 6: thermoplastic aromatic-ether aromatic-ester resin to which 5 parts by weight of triallyl isocyanurate were added, and which was irradiated with electron beam of 300 kGy.

Sample 7: Thermoplastic aromatic-ether aromatic-ester resin to which 5 parts by weight of triallyl isocyanurate were added.

The results of the above-described study of compression resistance are shown in FIG. 5. With sample 6 which underwent irradiation with electron beam and crosslinking treatment, compression distance was shorter than sample 5 composed of PTFE, and compression resistance was improved. Moreover, the compression distance of sample 7 composed of the same material as sample 6 but not irradiated with electron beam was at the same level as sample 5, thereby confirming that this effect is brought about by the crosslinking of thermoplastic resin associated with the irradiation of electron beam.

C) Study of Rigidity (Buckling Resistance)

A study of buckling resistance was conducted using the aforementioned samples 5 through 7. A slit of 3 mm length was made in rubber sheets of 0.5 mm thickness and A40 hardness which were fixed in place, and the respective samples 5 through 7 were inserted 10 mm from the distal end. Test subjects grasped with their fingers a part of the sample at a prescribed distance from the rubber sheet, and pushed the sample into the slit at a standard speed of 300-500 mm/second. The distance from the rubber sheet was adjusted at intervals of 1 cm, and the maximum distance when, the sample which was inserted into the slit was not bent (buckled) was treated as the insertable distance. There were three test subjects, and each conducted the study using each sample 5 through 7. The results are shown in FIG. 6.

As shown in FIG. 6, with respect to each of the test subjects, sample 6 had the longest insertable distance, demonstrating improved buckling resistance.

As described above, it was confirmed that the crosslinked part 11 had superior heat resistance, compression resistance and buckling resistance compared to parts which are not subjected to crosslinking treatment.

Figures 7, 8:
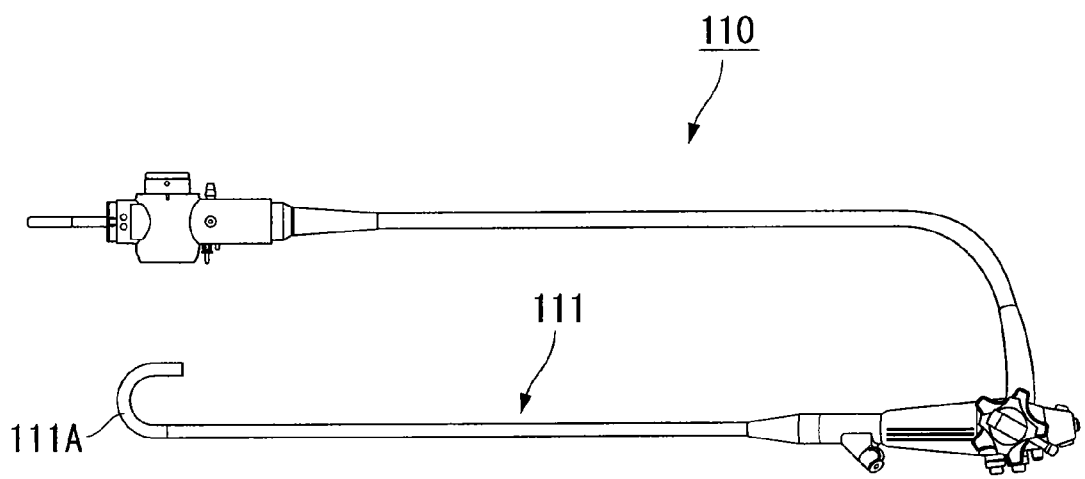
FIG. 7 is a figure which shows a state in which the endoscope is curved.
FIG. 8 is a table which shows study results pertaining to the insertability of a crosslinked part of this same medical treatment tool.

However, as these parameters have properties which conflict with the aforementioned insertability, it is difficult to have these parameters simultaneously coexist with insertability. Thus, in the present embodiment, the crosslinked part 11 is formed by conducting crosslinking treatment only in a region R1 of prescribed length from the distal end, which is exposed to high heat emitted from the treatment part 20 and treated tissue or the like during treatment. It is preferable to set the length of the crosslinked part 11 within a range of 2 to 10 mm from the distal end. The following study was conducted with respect to the insertability of the sheath 10 provided in this manner with the crosslinked part 11 only in a prescribed region on the distal end side As shown in FIG. 7, in imitation of a channel at a curvable site 111A of an endoscope 110 in which a curvable site 111A of an insertion part 111 is curved by curving manipulation, a tube made of PTFE with an inner diameter of 3 mm was formed in a ¼ arc shape with a radius of curvature of 40 mm, the aforementioned samples 5 and 6 as well as the below-mentioned samples 8 and 9 were passed through and within it, and the force required for pass-through was measured.

Sample 8: thermoplastic aromatic-ether aromatic-ester resin to which 5 parts by weight of triallyl isocyanurate were added, and which was irradiated with electron beam of 300 kGy in a region of 2 mm length from the distal end.

Sample 9: thermoplastic aromatic-ether aromatic-ester resin to which 5 parts by weight of triallyl isocyanurate were added, and which was irradiated with electron beam of 300 kGy in a region of 10 mm length from the distal end.

It should be noted that the inner diameter, outer diameter and length of samples 8 and 9 were identical to those of samples 5 through 7. Results are shown in FIG. 8.

FIG. 8 shows average values after conducting the study five times. The average pass-through force of sample 6 whose entirety had undergone crosslinking treatment was approximately the same as that of sample 5 of PTFE composition. In contrast, samples 8 and 9 which had been provided with the crosslinked part 11 only on the distal end side were both able to be passed through with a smaller pass-through force than samples 5 and 6, thereby demonstrating improved insertability.

According to the treatment tool 1 of the present embodiment, as a sheath 10 is provided which has a crosslinked part 11 in a region R1 of prescribed length on the distal end side, there occurs no melting or deformation even when the treatment part 20 and the treated tissue or the like emit high heat, and even when contact is made by the operating wire in the vicinity of the current-carrying, high-temperature treatment part 20, thereby enabling treatment to be safely conducted.

As compression resistance is increased in the crosslinked part 11, when tissue is seized by the snare wire 21 and pulled in toward the sheath 10 side, even if the snare wire 21 and the sheath 10 come into contact, and the distal end of the sheath 10 sustains compression in the axial direction, the pertinent compression can be suitably checked, and damage to the distal end of the sheath 10 can be prevented.

Moreover, as it is possible to form the crosslinked part 11 in a region of a portion of the sheath 10 merely by irradiating with ionizing radiation a desired region of a tube formed with mixed material in which thermoplastic resin and a crosslinking promoter are intermixed, the physical properties of a portion of the sheath can be easily enhanced without depending on troublesome and inefficient methods such as two-color molding or the joining of tubes of different material, as has previously been the case.

Next, a second embodiment of the present invention is described with reference to FIG. 9 and FIG. 10. The points of difference between the above-described treatment tool 1 and a treatment tool 41 of the present embodiment are the position and length of the crosslinked part. In the following description, the same code numbers are given to components common to the treatment tools of each embodiment which have been described above, and redundant description is omitted.

Figure 9:
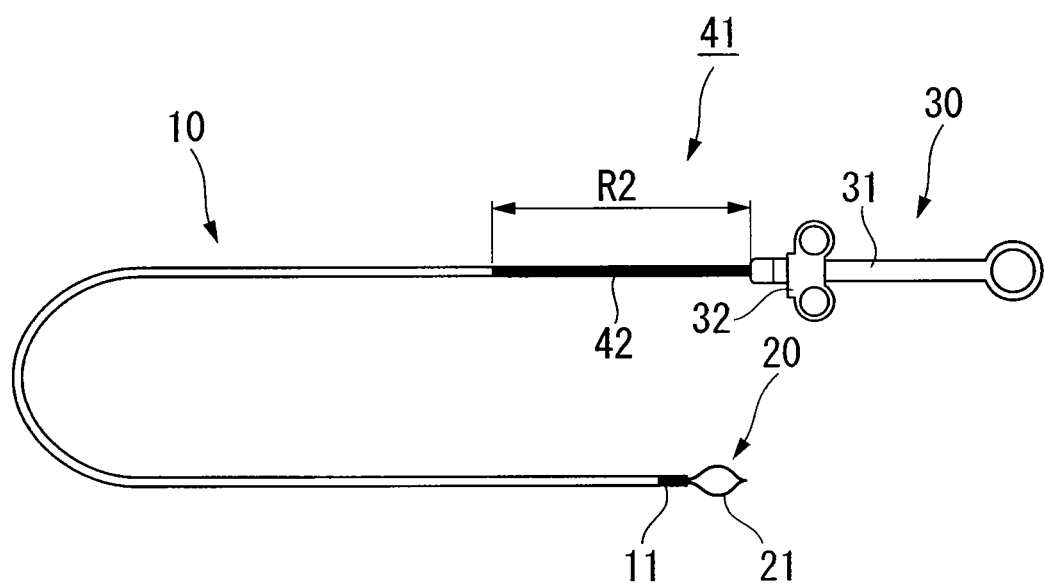
FIG. 9 is a figure which shows the medical treatment tool of a second embodiment of the present invention.

FIG. 9 is an overall view of the treatment tool 41. The treatment tool 41 is a treatment tool for an endoscope. With respect to the sheath 10, in addition to a crosslinked part 11 identical to the crosslinked part 11 of the first embodiment, a crosslinked part 42 is formed by irradiating with ionizing radiation a region R2 of prescribed length from the proximal end which is connected to the body 31.

The treatment tool 41 of the present embodiment is able to obtain the same effects as the treatment tool 1 of the first embodiment.

Figure 10:
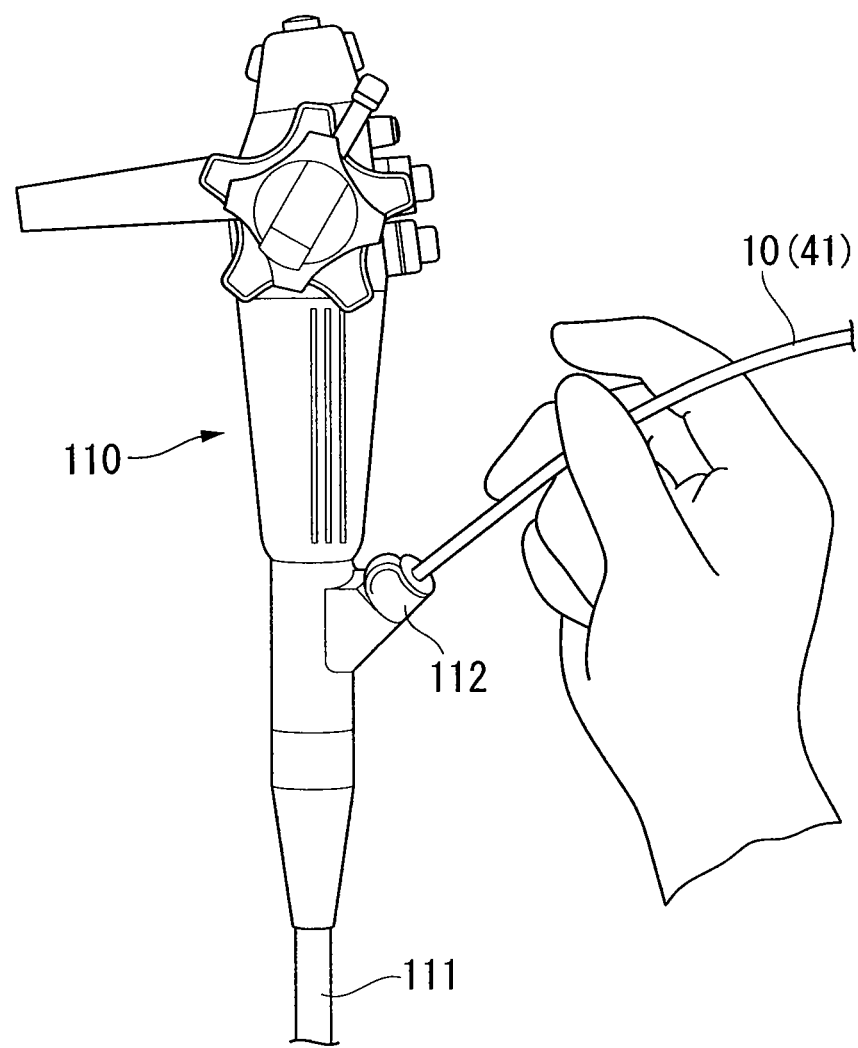
FIG. 10 is a figure which shows the operations for insertion of this same medical treatment tool into an endoscope.

As shown in FIG. 10, the treatment tool 41 is inserted from a channel plug port 112 of an endoscope 110, and treatment is conducted with projection of the distal end of the sheath 10 from the distal end of an insertion part 111. The lengthwise dimensions of the region R2 where the crosslinked part 42 is formed are set to a length such that only the crosslinked part 42 of the sheath 10 is exposed to the exterior of the endoscope 110 when treatment is conducted in the aforementioned state.

The exposed site is the region which is most susceptible to the force generated by the manipulation part 30. Accordingly, by enhancing the compression resistance of the pertinent region, it is possible to greatly improve the transmissibility with which the force generated by the manipulation part 30 is transmitted as force for use in treatment by the treatment part 20. By this means, according to the configuration of the treatment part, one obtains the advantages of improving tissue clamping force, improving tissue binding force, improving the incisiveness of tissue incisions, and enabling the sensation of tissue binding to be satisfactorily sensed by the operator.

Moreover, this exposed site is a region which is often grasped by the operator during the conduct of treatment to manipulate the treatment tool 41 forward and backward. Accordingly, by improving the buckling resistance and compression resistance of the pertinent region, it becomes possible to configure the treatment tool 41 to be more easily manipulable.

Next, a third embodiment of the present invention is described with reference to FIG. 11. The points of difference between the above-described treatment tools of the respective embodiments and a treatment tool 51 of the present embodiment are the position and length of the crosslinked part.

Figure 11:
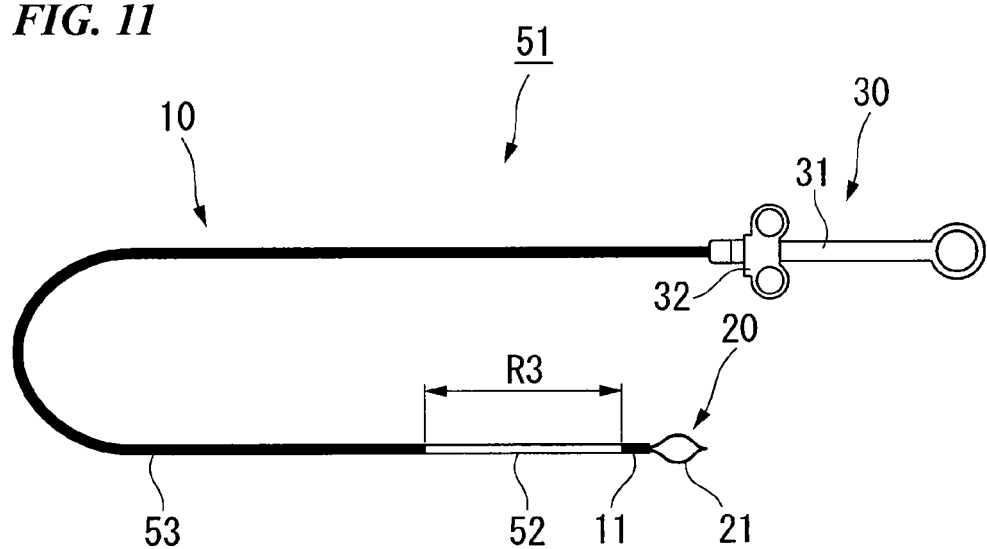
FIG. 11 is a figure which shows the medical treatment tool of a third embodiment of the present invention.

FIG. 11 is an overall view of the treatment tool 51. With respect to the sheath 10, only a region R3 of prescribed length on the proximal end side from the crosslinked part 11 of the distal end is left as a noncrosslinked region 52, and the entire region on the proximal end side from the noncrosslinked region 52 constitutes a crosslinked part 53.

The position and length of the region R3 left by the noncrosslinked region 52 are set so that it is situated at the curvable site 111A shown in FIG. 7 when the treatment tool 51 is inserted into a common endoscope 110, and the distal end of the sheath 10 projects from the endoscope 110. Accordingly, as the insertability of the region R3 greatly affects the manipulability of the treatment tool 51 when it is inserted into the endoscope 110, it is possible to maintain the insertability of the treatment tool 51 at a high level by setting the region R3 in the aforementioned manner.

It is preferable that the length of the region R3 constituting the noncrosslinked region 52 be roughly on the order of 100 to 150 mm, and this may be appropriately modified according to the total length of the treatment tool 51 and design values and the like of the endoscope 110.

The crosslinked part 53 of the proximal end side is set so as to be longer than the region which projects from the channel plug port 112 when the treatment tool 51 has been inserted into the endoscope 110. As shown in FIG. 10, when the treatment tool 51 is inserted into the endoscope 110 from the channel plug port 112, a region of the sheath 10 farther toward the distal end side than the crosslinked part 42 is grasped, and is inserted into the channel. Accordingly, by forming a crosslinked part 53 which extends farther toward the distal end side than the crosslinked part 42, it is possible to suitably prevent buckling and the like not only during manipulation at the time of treatment, but also when the treatment tool 51 is being inserted into the endoscope 110. Moreover, as the compression resistance of the crosslinked part 42 is enhanced, it is possible to greatly improve the transmissibility to the treatment part 20 of the aforementioned manipulation force generated by the manipulation part 30.

According to the treatment tool 51 of the present embodiment configured in the foregoing manner, by providing noncrosslinked region 52 and crosslinked part 53, insertion into the endoscope can be appropriately conducted without significant impairment of insertability into the endoscope, and a suitably manipulable treatment tool can be obtained.

Preferred embodiments of the present invention have been described above, but the present invention is not limited to these embodiments. Additions, omissions, substitutions, and other modifications can be made within a scope that does not deviate from the intent of the present invention.

For example, with respect to each of the foregoing embodiments, the case has been described where the crosslinked part is established by irradiating the entirety of a specified region with ionizing radiation, but it is also acceptable to instead form the crosslinked part by continuously forming a crosslinked region in microscopic units in the axial direction within the specified region.

Figure 12:
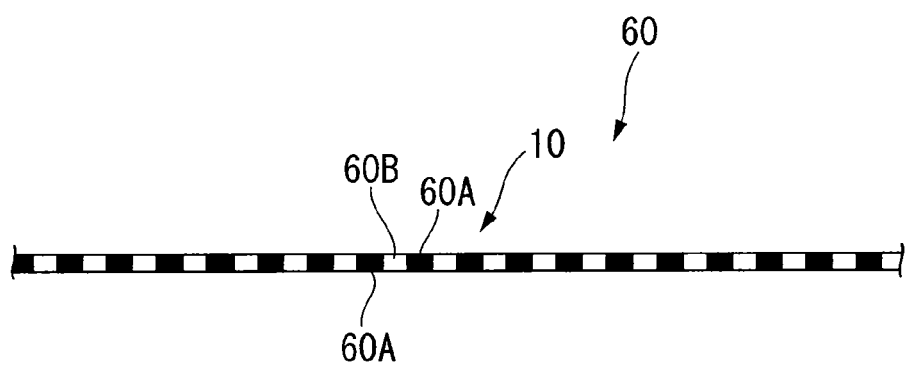
FIG. 12 is a figure which shows a crosslinked part in a medical treatment tool of a variation of the present invention.
Figure 13:
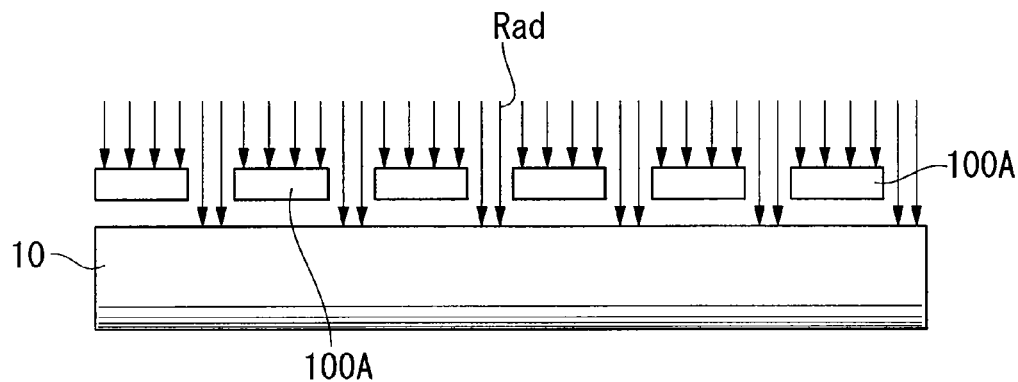
FIG. 13 is a figure which shows the operations for forming this same crosslinked part.

FIG. 12 shows another example of a crosslinked part. A crosslinked part 60 is formed by continuously forming unit-crosslinked parts 60A with dimensions on the order of several mm in the axial direction of the sheath 10. As shown in FIG. 13, this type of crosslinked part 60 can be formed by covering the sheath 10 with a row of band-like shields 100A placed at equal intervals, and by conducting irradiation with the ionizing radiation Rad. Instead of the band-like shields 100A, it is also acceptable to use shields of annular or other shape.

Even when the crosslinked part is formed in this manner, it is possible to obtain the effects described above. Furthermore, as an advantage obtained when conducting continuous alternating placement of such unit-crosslinked parts 60A with interposition of noncrosslinked regions, one may cite the point that secondary processing of the sheath is facilitated.

That is, although the crosslinked part enhances heat resistance, it worsens bindability with other members by thermal formation, welding or the like. Moreover, due to the increased rigidity, ease of deformation declines, and bindability with other members by press fitting or the like also declines. However, if noncrosslinked regions remain in the localized manner described above, it is possible to facilitate the conduct of secondary processing such as the aforementioned adhesion using the pertinent noncrosslinked regions. Accordingly, with respect to sheaths pertaining to such variations, it is possible to assure the ease of secondary processing while enhancing overall heat resistance, rigidity, compression resistance, etc.

It is acceptable to appropriately modify the axial dimensions of the unit-crosslinked parts 60A as well as the axial dimensions of the noncrosslinked regions 60B interposed between adjacent unit-crosslinked parts 60A. Accordingly, by modifying the ratio of the axial dimensions of the unit-crosslinked parts 60A and unit-noncrosslinked regions 60B, the overall flexibility and rigidity of the crosslinked part 60 can be controlled within a desired range to a certain extent.

Figure 14A:
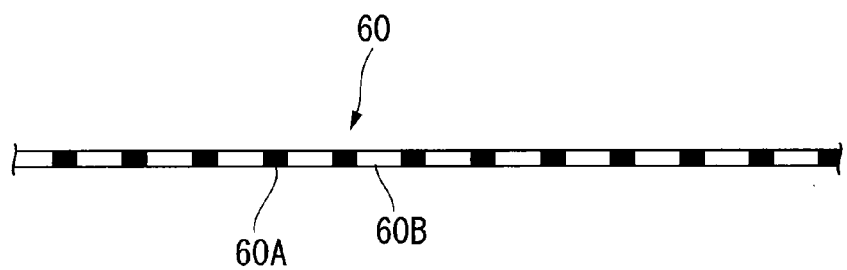
FIG. 14A and FIG. 14B are figures which respectively show crosslinked parts in a medical treatment tool of a variation of the present invention.

For example, as shown in FIG. 14A, when the dimensional ratio of the unit-crosslinked parts 60A and unit-noncrosslinked regions 60B in the axial direction are set to 1:2, it is possible to make a crosslinked part which has better insertability than one formed with a dimensional ratio of 1:1.

Figure 14B:
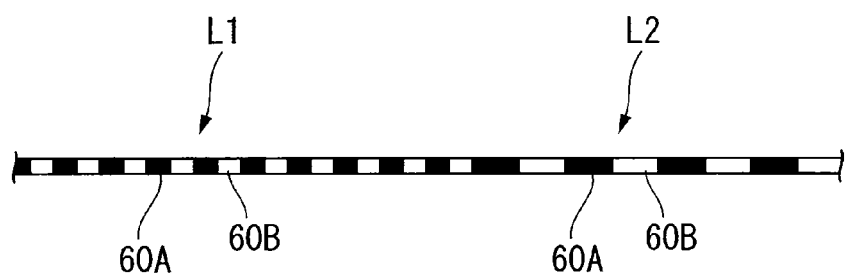

It is also acceptable to vary the pertinent dimensional ratios of the crosslinked part on the distal end side and the crosslinked part on the proximal end side. In this case, as in the variation shown in FIG. 14B, one may adopt a configuration where the dimensional ratios are identical while the axial dimensions per unit differ, as when the dimensional ratio of a region L1 is 1:1 while the dimensional ratio of an adjacent region L2 is 2:2.

In addition, if one considers each unit-crosslinked part as a single crosslinked part, a mode wherein a crosslinked part is formed with the aforementioned configuration over the entire length of the sheath also falls within the scope of the present invention. If one adopts this configuration, it is possible to satisfactorily maintain a better insertability than in the case where the entire sheath is simply subjected to crosslinking treatment.

Figure 15:
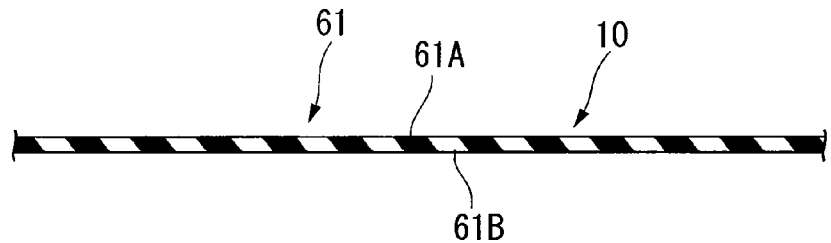
FIG. 15 is a figure which shows a crosslinked part in a medical treatment tool of a variation of the present invention.

Moreover, it is also acceptable to provide a crosslinked part 61 of prescribed length by helically forming a single or multiple linear unit-crosslinked part(s) 61A on the outer circumferential face of the sheath 10 as shown in FIG. 15. This type of crosslinked part 61 can be easily formed by winding a spiral shield around the sheath 10. When this is done, external appearance resembles that of the aforementioned crosslinked part 60, but in the case of the crosslinked part 61, a unit-crosslinked part 61A and -noncrosslinked region 61B are continuously provided in the axial direction of the sheath 10, thereby enabling insertability and buckling resistance to coexist more easily.

Otherwise, it is also acceptable to multiply form linear narrow crosslinked parts in rows in the circumferential direction of the sheath and approximately parallel in the axial direction of the sheath. With respect to the aforementioned unit-crosslinked parts, by identically forming linear narrow crosslinked parts, it is possible to adopt a balance of insertability and compression resistance.

Figure 16:
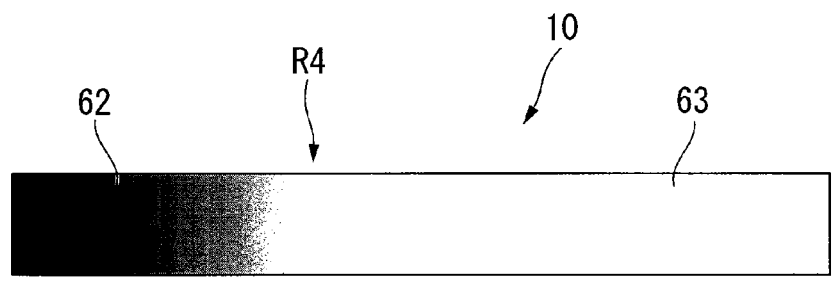
FIG. 16 is a figure which shows a crosslinked part in a medical treatment tool of a variation of the present invention.
Figure 17:
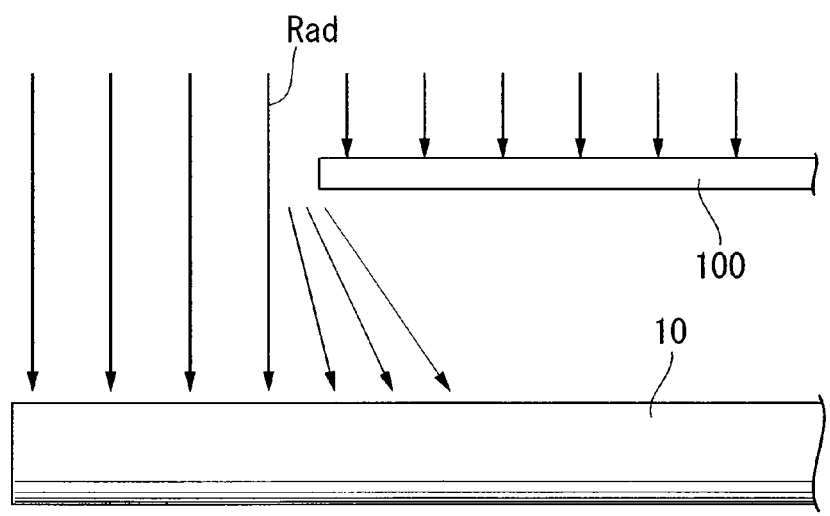
FIG. 17 is a figure which shows the operations for forming this same crosslinked part.

As in the variation shown in FIG. 16, it is also acceptable to configure the sheath 10 so that it has a transition region R4 where the proportion of crosslinking (degree of crosslinking) gradually changes at the boundary of the crosslinked part 62 and noncrosslinked region 63. When this type of crosslinked part 62 is formed, as shown in FIG. 17, irradiation with ionizing radiation Rad is conducted in a state where the distance between the shield 100 and the sheath 10 is widened. When this is done, as a result of diffraction and the like, a portion of the ionizing radiation Rad enters between the shield 100 and the sheath 10, and a certain degree of crosslinking occurs due to the ionizing radiation Rad which has entered. As this degree of crosslinking increases as the crosslinked part 62 is approached, it is possible to form the transition region R4 in the manner shown in FIG. 16. The degree of transition in the transition region R3 can be appropriately adjusted by adjusting the distance between the sheath 10 and the shield 100.

When the sheath 10 is configured so as to have the transition region R4, flexibility and rigidity gradually change from the crosslinked part 62 to the noncrosslinked region 63, thereby enabling configuration of a treatment tool which has a better sense of use.

Furthermore, with respect to each of the aforementioned embodiments, the case was described where the member inserted into the body is a treatment tool formed only by a sheath, but instead of this, it is also acceptable to adopt a treatment tool configuration where the pertinent member is formed from a coil sheath composed of metal wire and a sheathing tube of thermoplastic resin which covers the outer circumferential face of the coil sheath, and where the crosslinked part is provided on this sheathing tube. One example is shown below.

The sample A and sample B shown below were prepared.

Sample A: a coil sheath with a loop inner diameter of 1.0 mm and outer diameter of 2.0 mm was covered with a sheathing tube (of 0.15 mm wall thickness) made of thermoplastic aromatic-ether aromatic-ester resin to which 5 parts by weight of triallyl isocyanurate were added.

Sample B: the same coil sheath and sheathing tube as sample A were used, and irradiation with ionizing radiation of 300 kGy was conducted in a state where the coil sheath was fitted into the sheathing tube.

The aforementioned sample A and sample B (each with a length of 150 mm) were supported by two supports set at an interval of 45 mm, and measurement was conducted of the force necessary to cause a 10 mm indentation deformation at the center point of the supports at a pressing speed of 50 cm/minute.

Figures 18, 19:
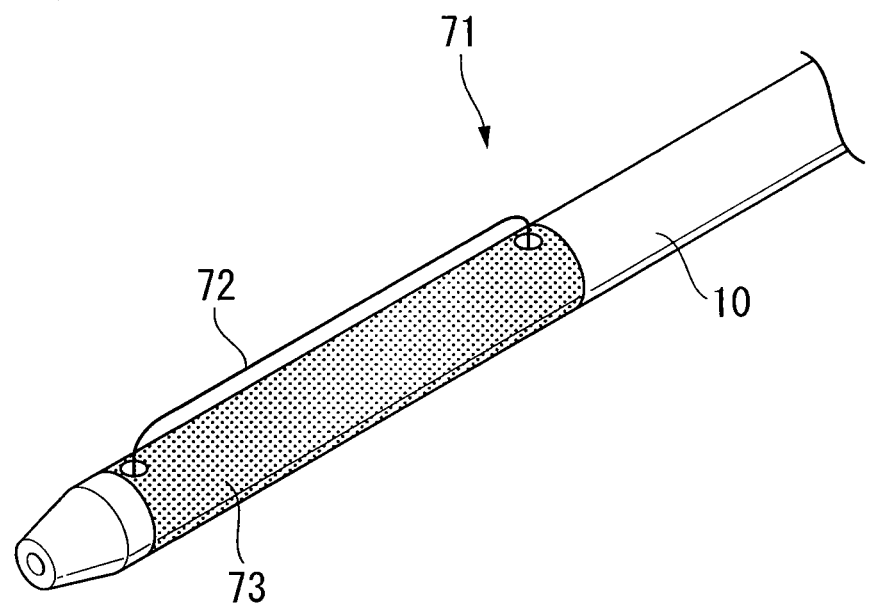
FIG. 18 is a table which shows the results of a study of rigidity of the medical treatment tool of a variation of the present invention.
FIG. 19 is a figure which shows a treatment part and a crosslinked part pertaining to the medical treatment tool of a variation of the present invention.

FIG. 18 is a table which shows the results of the aforementioned study. The force required to cause indentation deformation is greater with sample B which was subjected to crosslinking by electron beam, thereby demonstrating improved rigidity.

Furthermore, in each of the foregoing embodiments, the description concerned the case of a snare wire energized by high-frequency current in the treatment part, but the treatment tool of the present invention has no particular limitations in terms of the form, configuration, or application of the treatment part. Accordingly, instead of a snare wire, it is possible to apply the configuration of the present invention to treatment tools having various types of treatment parts such as a forceps or knife. In such cases, when the treatment tool adopts a configuration which does not emit heat, it is not necessarily required to form a crosslinked part on the distal end side of the sheath to raise heat resistance. Moreover, as with a so-called papillotomy knife 71 like that shown in FIG. 19, when a configuration is adopted where there is a possibility of imparting effects to the outer circumferential face of the sheath 10 by a treatment part 72 or heat or the like generated during treatment, it is acceptable to form a crosslinked part 73 in a region of specified scope where the possibility of contact by the treatment part 72 exists at the distal end side of the sheath 10.

Each of the foregoing embodiments illustrates the case where a crosslinked part is formed at the desired site by irradiating a portion of the sheath with ionizing radiation in a state where it is covered with a shield, but the method for forming a crosslinked part at a desired site is not limited thereto. For example, it is also acceptable to mold a sheath by two-color molding using mixed material and thermoplastic resin that does not contain a crosslinking promoter, irradiate the entire outer circumferential face of this sheath with ionizing radiation, and cause crosslinking only in the region(s) composed of mixed material to establish the crosslinked part(s) at the desired site(s). When this is done, as the entirety of the outer circumferential face of the sheath is irradiated with ionizing radiation, it is possible not only to form crosslinked parts, but also to sterilize the sheath, thereby enabling simplification of the manufacturing process. Moreover, as the mixed material and the thermoplastic resin that does not contain a crosslinking promoter include the identical thermoplastic resin, there is no need to take account of the compatibility of mated resins as in ordinary two-color molding using different resin materials, thereby facilitating the molding of the sheath.

With respect to the formation of crosslinked parts, it is possible to appropriately combine and optimize the configurations and methods of the respective embodiments and variations described above. The present invention is not limited by the foregoing descriptions, and is only limited by the scope of the appended claims.

The invention claimed is:

1. A treatment tool which is configured to be used with an endoscope and is inserted into a body cavity for use, comprising:
   a wire shaped manipulation member having a treatment part with a distal end thereof which is configured to perform a treatment procedure to a subject by applying thermal energy to the subject;
   a tubular shaped sheath composed of thermoplastic resin having an insertion path;
   a manipulation part attached to a proximal end of the manipulation member so as to move the treatment part with respect to the sheath in order to perform the treatment procedure; wherein
   the sheath is configured such that the manipulation member is inserted into the insertion path and that the treatment part protrudes from a distal end of the sheath,
   the distal end of the sheath including:
      a non-crosslinked part, wherein the thermoplastic resin is not crosslinked, is situated at a position where the sheath protrudes from a distal end of a channel of the endoscope, and
      a crosslinked part, at a more distal end side of the sheath than the noncrosslinked part, formed by crosslinking the thermoplastic resin of a contact part which is contacted by the treatment part, said crosslinked part protruding from the distal end of the sheath, when the treatment procedure is performed by the treatment part.

2. The treatment tool according to claim 1, which further comprises a power supply part that supplies high-frequency current to said treatment part, and wherein said crosslinked part is provided in a prescribed range of length from the end of a sheath on a treatment part side.

3. The treatment tool according to claim 1, wherein
   a length of the crosslinked part within a range of 2 to 10 mm from the distal end of the sheath.

4. The treatment tool according to claim 1, wherein the crosslinked part is provided in a prescribed range of length from the end of the sheath on the treatment part side and in a prescribed range of length from the end of the sheath on said manipulation part side, and wherein
   when the treatment tool is inserted into the endoscope having a curvable insertion part, and when the distal end of the sheath projects out from the distal end of the endoscope, only the non-crosslinked region is located at a curvable site of the insertion part.

5. The treatment tool according to claim 1, wherein the sheath has a non-crosslinked region where the thermoplastic resin is not crosslinked, and the crosslinked part has a transition region in at least a portion of the boundary with the non-crosslinked region, where the degree of crosslinking of the thermoplastic resin gradually decreases toward the non-crosslinked region.

6. A treatment tool which is configured to be used with an endoscope and is inserted into a body cavity for use, comprising:
   a wire shaped means having a treatment means with a distal end thereof which performs a treatment procedure to a subject by applying thermal energy to the subject;
   a tubular means composed of thermoplastic resin having an insertion path;
   a manipulation means attached to a proximal end of the wire shaped means so as to move the treatment means with respect to the tubular means in order to perform the treatment procedure; wherein
   the tubular means is configured such that the manipulation means is inserted into the insertion path and the treatment means protrudes from a distal end of the tubular means
   the distal end of the tubular means including:
      a non-crosslinked means, wherein the thermoplastic resin is not crosslinked, situated at a position where the sheath protrudes from a distal end of a channel of the endoscope, and
      a crosslinked means, at a more distal end side of the tubular means than the non-crosslinked means, formed by crosslinking the thermoplastic resin of a contact means which is contacted by the treatment means and which protrudes from the distal end of the tubular means when the treatment procedure is performed by the treatment means.

* * * * *